United States Patent [19]
Coleman et al.

[11] Patent Number: 4,983,120
[45] Date of Patent: Jan. 8, 1991

[54] METHOD AND APPARATUS FOR CONSTRUCTING AN ORTHODONTIC APPLIANCE

[75] Inventors: Angus C. Coleman, Upland; Scott G. Newhart, Los Angeles, both of Calif.

[73] Assignee: Specialty Appliance Works, Inc., Atlanta, Ga.

[21] Appl. No.: 192,909

[22] Filed: May 12, 1988

[51] Int. Cl.$^5$ ................................................. A61C 3/00
[52] U.S. Cl. ....................................................... 433/24
[58] Field of Search .......................................... 433/24

[56] References Cited

U.S. PATENT DOCUMENTS 3,906,634 9/1975 Aspel ..................................... 433/24
3,949,478 4/1976 Schinhammer ....................... 433/24
4,183,141 1/1980 Dellinger et al. ...................... 433/24

Primary Examiner—John J. Wilson
Attorney, Agent, or Firm—Marjama & Pincelli

[57] ABSTRACT

A method and apparatus for constructing an orthodontic applicance. The method includes the forming of a model of a patient's malocclusion. The teeth are separated and teeth are placed back in their malooclusion position on a base support. The teeth are moved directly from the malocclusion position to the prescribed ideal form. A tool is provided which can assist in establishing the arch form, placing the brackets on the model teeth in accordance with the desired arch form and determining the wire arch form.

4 Claims, 9 Drawing Sheets

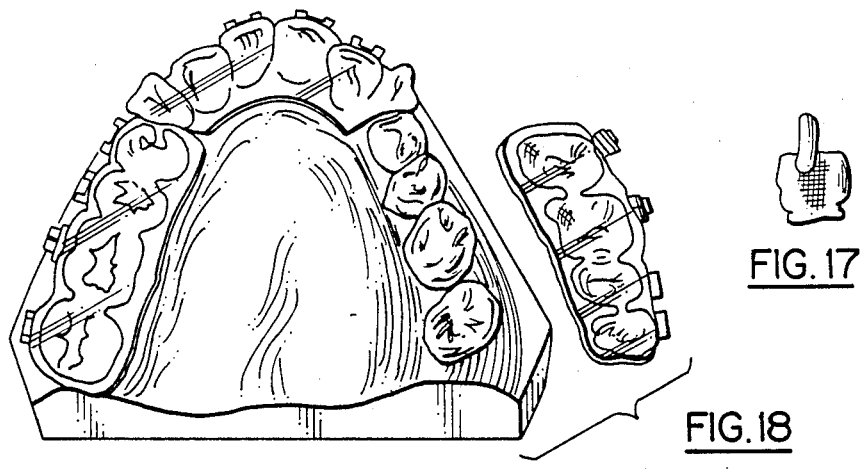

CASE ANALYSIS

PATIENT NAME: JANE DOE    C 2000

| TOOTH | MALOCCLUSION | | RxOCCLUSION | | DEGREE CHANGE | |
|---|---|---|---|---|---|---|
| UPPER | TQ | ANG | TQ | ANG | TQ | ANG |
| CENTRAL-R | +7 | +3 | | | | |
| CENTRAL-L | +8 | +3 | | | | |
| LATERAL-R | +5 | +7 | | | | |
| LATERAL-L | +6 | +8 | | | | |
| CUSPID-R | -8 | +9 | | | | |
| CUSPID-L | -5 | +9 | | | | |
| LOWER | | | | | | |
| CENTRAL-R | -3 | -4 | | | | |
| CENTRAL-L | 0 | +1 | | | | |
| LATERAL-R | -4 | -8 | | | | |
| LATERAL-L | -4 | -2 | | | | |
| CUSPID-R | -9 | -1 | | | | |
| CUSPID-L | -9 | -3 | | | | |

OTHER CONSIDERATIONS

| | MALOCCLUSION | RxOCCLUSION | CHANGE |
|---|---|---|---|
| OVERSET | 7MM | | |
| OVERBITE | 4MM | | |
| INTERCANINE WIDTH (MANDIBULAR) | 23MM | | |
| INTERMOLAR WIDTH (MANDIBULAR) | 40MM | | |
| DENTAL MIDLINE | ON | | |

TABLE A

CASE ANALYSIS

PATIENT SIZE: JANE DOE    C 2000

| TOOTH | MALOCCLUSION | | RxOCCLUSION | | DEGREE CHANGE | |
|---|---|---|---|---|---|---|
| UPPER | TQ | ANG | TQ | ANG | TQ | ANG |
| CENTRAL-R | +1 | +3 | +15 | +5 | +8 | +2 |
| CENTRAL-L | +8 | +3 | +14 | +5 | +6 | +2 |
| LATERAL-R | +5 | +7 | +10 | +8 | +5 | +1 |
| LATERAL-L | +6 | +8 | +10 | +8 | +4 | +2 |
| CUSPID-R | −8 | +5 | −4 | +9 | +4 | +4 |
| CUSPID-L | −5 | +9 | −2 | +9 | +3 | +0 |
| LOWER | | | | | | |
| CENTRAL-R | −3 | −4 | +1 | 0 | +4 | +4 |
| CENTRAL-L | 0 | +1 | +1 | 0 | +1 | −1 |
| LATERAL-R | −4 | −8 | +1 | +3 | +5 | +11 |
| LATERAL-L | −4 | −2 | +1 | +4 | +5 | +6 |
| CUSPID-R | −9 | −1 | −7 | +5 | +2 | +6 |
| CUSPID-L | −9 | −3 | −6 | +4 | +3 | +7 |

OTHER CONSIDERATIONS

| | MALOCCLUSION | RxOCCLUSION | CHANGE |
|---|---|---|---|
| OVERSET | 7MM | 1MM | −6MM |
| OVERBITE | 4MM | 1MM | −3MM |
| INTERCANINE WIDTH (MANDIBULAR) | 23MM | 25MM | +2MM |
| INTERMOLAR WIDTH (MANDIBULAR) | 40MM | 40MM | NO CHANGE |
| DENTAL MIDLINE | ON | ON | NO CHANGE |

TABLE B

METHOD AND APPARATUS FOR CONSTRUCTING AN ORTHODONTIC APPLIANCE

BACKGROUND OF THE INVENTION

The present invention relates to Orthodontics and more particularly to a method and apparatus for precisely locating orthodontic brackets on a patient's teeth.

Various treatments exist for the treatment of an orthodontic malocclusion. In one method, a plaster cast of the malocclusion is obtained. The teeth are then separated and individually placed on a base support in their prescribed position. Thereafter, brackets are individually placed on the teeth. The brackets, through known transfer techniques, are then placed on the patient's teeth. The length of the orthodontic procedure is highly dependent upon the accuracy of placement of the brackets and severity of the patient's teeth. The accurate placement of brackets in the prior art has been difficult to maintain. Additionally, in the procedures of the prior art, no consideration has been given to whether or not the teeth can efficiently move from the maloccluded position to the ideal form. As a consequence, in some instances, the prescribed form cannot be easily reached if at all.

Applicants have invented an improved method and apparatus whereby the degree of accuracy of placing the teeth on the ideal model and back onto the malocclusion can be obtained with extreme accuracy. Additionally, Applicants have developed a method that accounts for movement from the malocclusion to its ideal form.

SUMMARY OF THE INVENTION

In one aspect of the present invention, there is provided a method of constructing an orthodontic appliance comprising the steps of:
  forming a model of a patient's malocclusion;
  separating said teeth from the model and placing the teeth back in the malocclusion positions on a base support whereby the teeth are capable of being manipulated;
  moving the teeth to their prescribed positions;
  establishing the desired arch form for the teeth; and
  placing orthodontic brackets on said teeth using said desired arch form.

In another aspect of the present invention, there is provided an apparatus for securing orthodontic brackets to model teeth. The apparatus is provided with a blade form having an outer peripheral edge which has a configuration which matches the ideal arch form. The arch form is capable of establishing the ideal arch form, placing the brackets on model teeth and determining the ideal arch wire form.

DESCRIPTION OF THE DRAWINGS

FIG. 17 is a back view of a bracket with filler material on its base;

FIG. 18 illustrates one method whereby the brackets may be taken from the malocclusion model for later transposing to the patient.

DETAILED DESCRIPTION OF THE INVENTION

Figure 1:
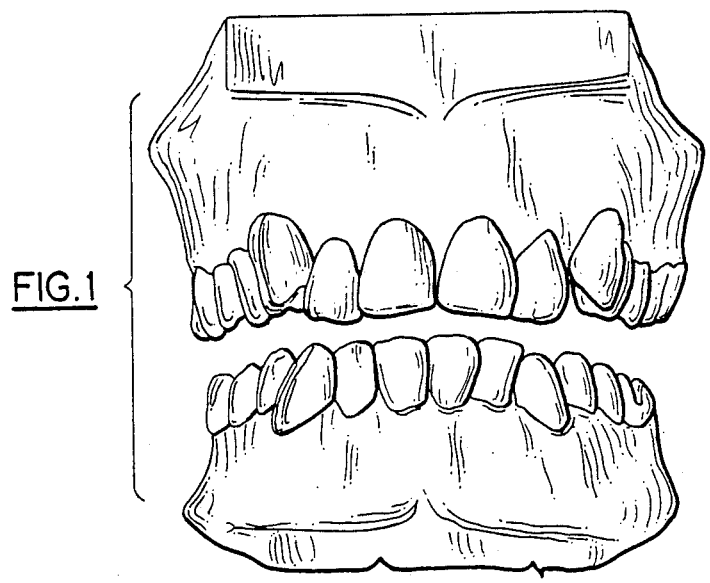
FIG. 1 is a front elevational view of a plaster cast of a malocclusion.

In accordance with the present invention, a reproduction in artificial stone, or in any other material desired, of the malocclusion 10 as illustrated in FIG. 1 is made. The obtaining of a malocclusion is a common procedure in the prior art and any desired procedure in the prior art may be used in the present invention to obtain malocclusion 10. A locating groove 12 is provided in each tooth upon which an orthodontic bracket is to be placed. Locating groove 12 is formed in a substantially vertical direction with respect to the longitudinal axis of the tooth and provides a well-defined seat 14. In the particular embodiment illustrated, locating groove 12 takes the form of generally a cylindrical bore with a substantially flat base. The providing of well-defined seat 14 helps assure proper locating of an orthodontic bracket to be placed on the tooth which is described in more detail later on. The positioning of the locating 12 groove in a substantially vertical direction assists in removing a silicone tray which is used later in the procedure. As is customly done in the art, a reproduction of the maxillary and mandibulary malocclusion is provided. Accordingly, malocclusion 10 comprises a maxillary malocclusion 16 and a mandibular malocclusion 18.

Figure 2:
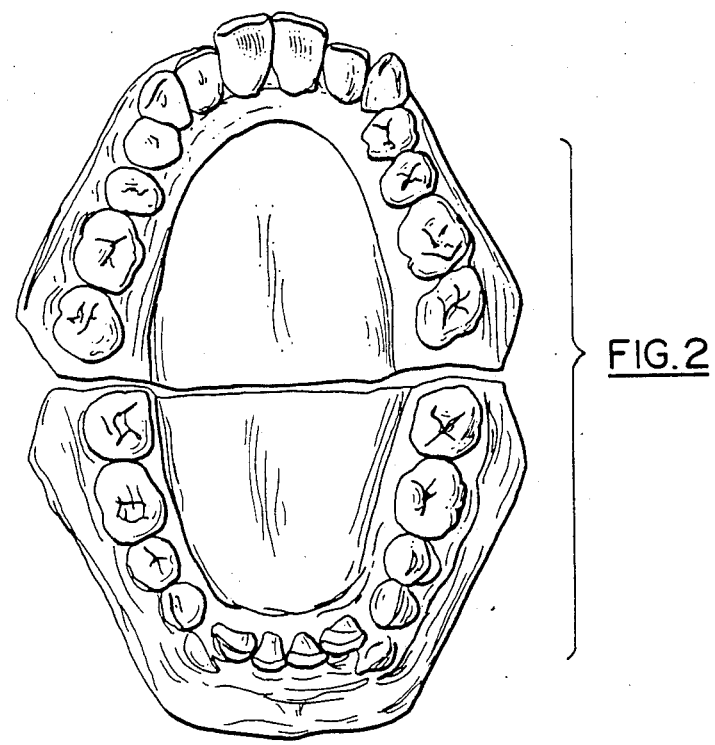
FIG. 2 is a top view of a plaster model copy of the patient's malocclusions illustrated in FIG. 1.
Figure 3:
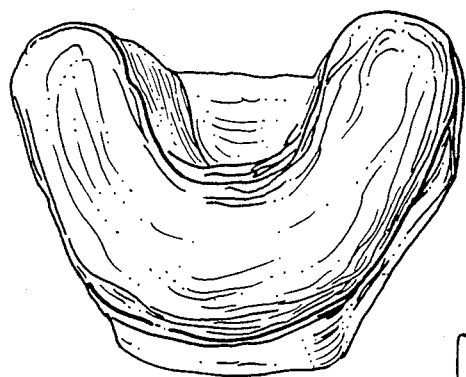
FIG. 3 is a perspective view of a silicone putty tray formed over the model of FIG. 2.
Figure 3A:
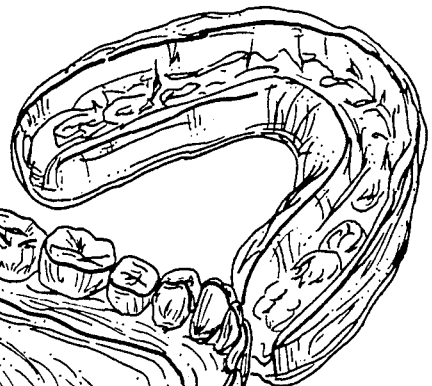
FIG. 3A is a perspective view of the model and tray of FIG. 3 with the tray removed.
Figure 6:
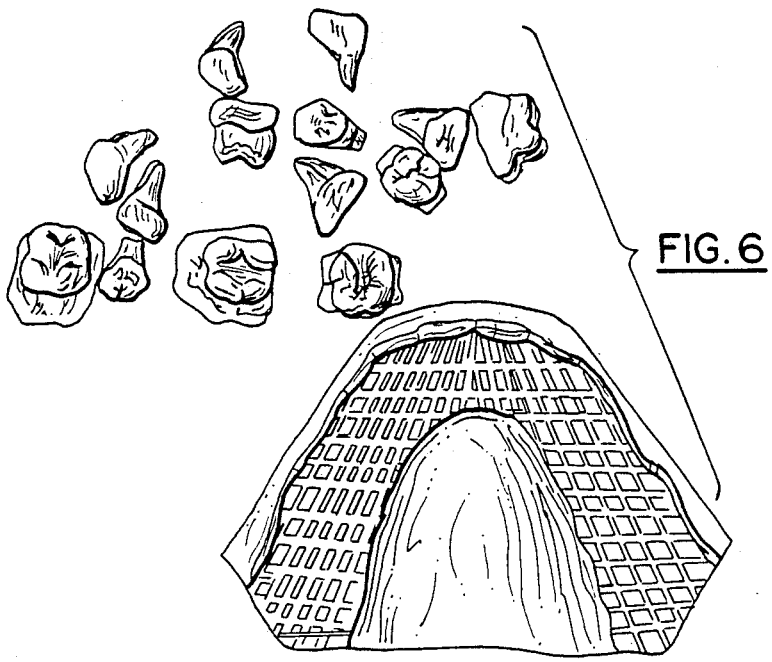
FIG. 6 illustrates a top plan view of one of the models of FIG. 3 wherein the teeth have been removed from the base portion and individually separated.

Due to the nature of the orthodontic procedure of the present invention, a duplicate model of the malocclusion 10 is made so as to provide a maxillary malocclusion model 20 and a mandibular malocclusion model 22 as illustrated in FIG. 2. Also, as illustrated in FIGS. 3 and 3A, silicone putty trays 24, 26 are provided over the entire malocclusion models 20, 22. The silicone trays 24, 26 are made such that at least a portion of the upper end 28 of each tray contacts the labial vestibules and some portion of the palate or the tongue area of the lower is incorporated. These upper ends 28 will serve to relocate the trays 24, 26 at a later time. Locating lines 29 are formed the tray and models as illustrated in FIG. 6. These lines are used to assist in realigning the trays and models. This can simply be made by a pen or other writing or marking instrument.

Figure 9:
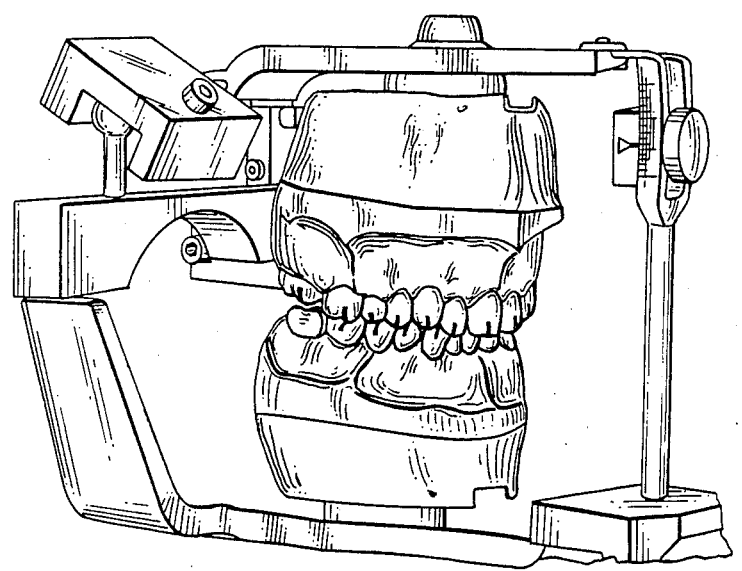
FIG. 9 illustrates the waxed models of FIG. 7 mounted on an articulator in their original malocclusion positions.
Figure 10:
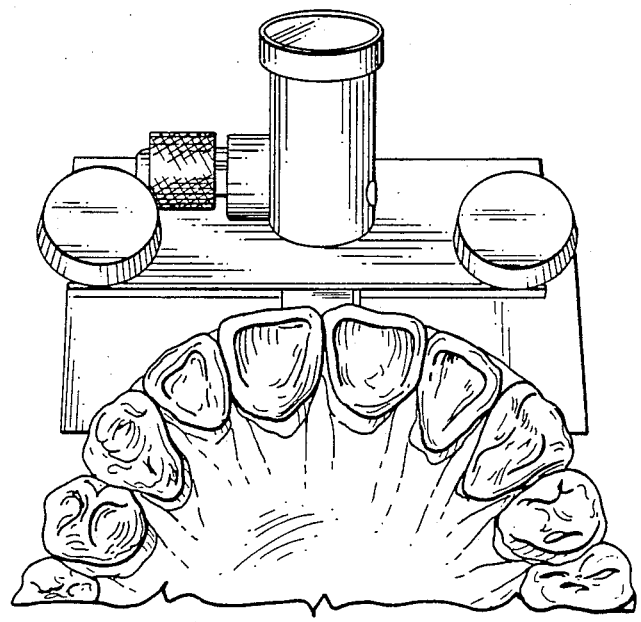
FIG. 10 is a top plan view illustrating one of the wax malocclusion models in their ideal shape and the tool used to establish the desired arch wire form.
Figure 11:
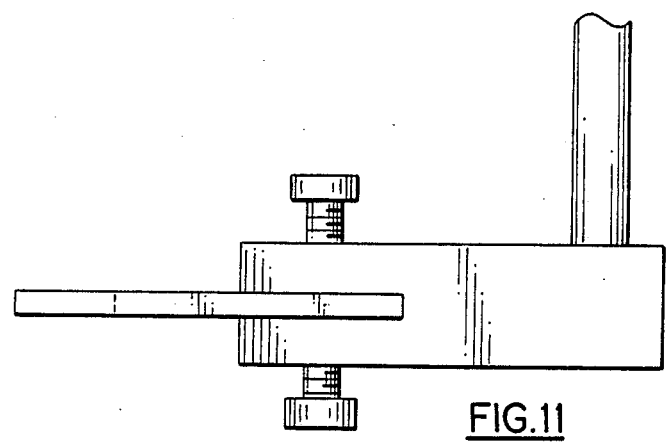
FIG. 11 is side view of the tool illustrated in FIG. 10.
Figure 11A:
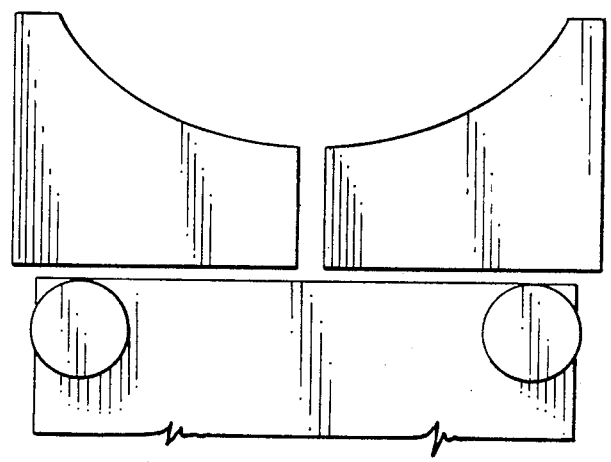
FIG. 11A illustrates the tool of FIG. 8 disassembled.

The models 20, 24 are mounted on a device capable of measuring certain features of the malocclusion (see FIG. 9). An example of one such device is the T.A.R.G. device sold by the Ormco Corporation. Each tooth is then identified by numbering each tooth and locating the long axis thereon. The long axis aids in setting the prescribed arrangement set forth by the orthodontist as well as providing a reference line for measuring the various degrees of malocclusion. At this point, various structural dimensions are measured using the T.A.R.G. device and recorded. For example, the angulation relative to the vertical and degree of labial crown torque is measured on each anterior tooth the distance between the canines is measured as this can provide the corners of the mouth of the patient which is very useful in obtaining the ideal prescription, and the distance between the central fossae of the first molar. It is, of course, understood that any other characteristic dimensions may be taken as desired at this time. The following table A illustrates a sample of the measurements taken.

TABLE A

| CASE ANALYSIS PATIENT NAME: JANE DOE c 2000 | | | | | | |
|---|---|---|---|---|---|---|
| | MALOC-CLUSION | | R$_x$OCCLUSION | | DEGREE CHANGE | |
| TOOTH | TQ | ANG | TQ | ANG | TQ | ANG |
| UPPER | | | | | | |
| CENTRAL-R | +7 | +3 | | | | |
| CENTRAL-L | +8 | +3 | | | | |
| LATERAL-R | +5 | +7 | | | | |
| LATERAL-L | +6 | +8 | | | | |
| CUSPID-R | −8 | +9 | | | | |
| CUSPID-L | −5 | +9 | | | | |
| LOWER | | | | | | |
| CENTRAL-R | −3 | −4 | | | | |
| CENTRAL-L | 0 | +1 | | | | |
| LATERAL-R | −4 | −8 | | | | |
| LATERAL-L | −4 | −2 | | | | |
| CUSPID-R | −9 | −1 | | | | |
| CUSPID-L | −9 | −3 | | | | |

| OTHER CONSIDERATIONS | | | |
|---|---|---|---|
| | MALOC-CLUSION | R$_x$OCCLUSION | CHANGE |
| OVERSET | 7 mm | | |
| OVERBITE | 4 mm | | |
| INTERCANINE WIDTH (MANDIBULAR) | 23 mm | | |
| INTERMOLAR WIDTH (MANDIBULAR) | 40 mm | | |
| DENTAL MIDLINE | ON | | |

Figure 5:
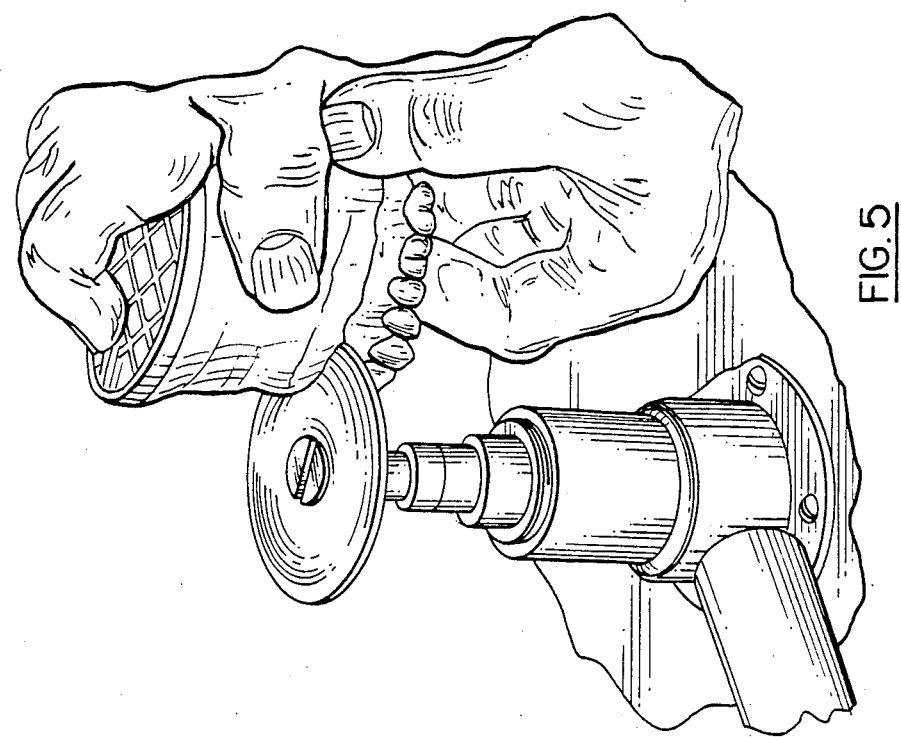
FIG. 5 illustrates how the teeth may be separated from the model of FIG. 2.
Figure 4:
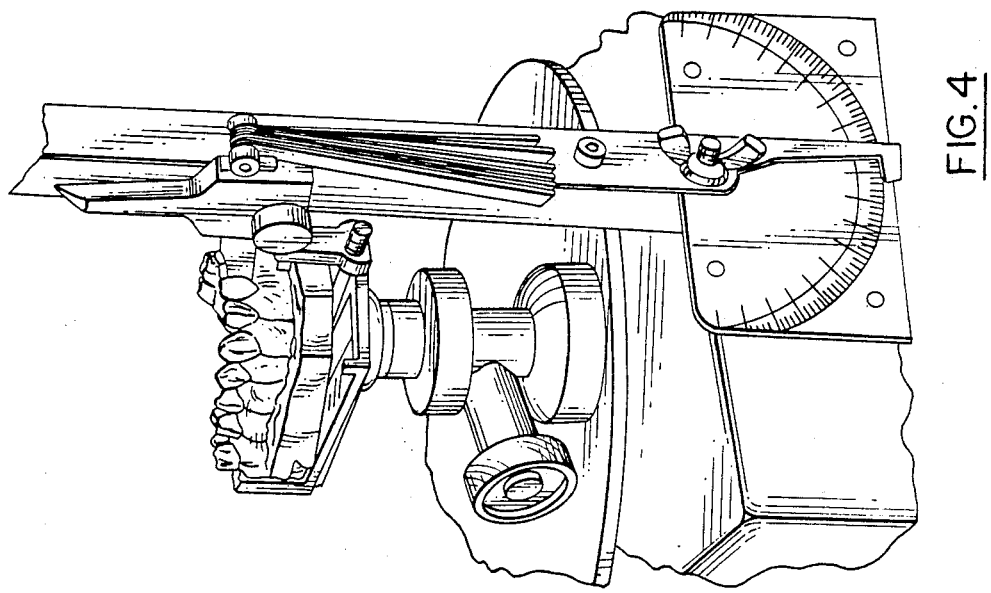
FIG. 4 is an elevational view of a device used to obtain tooth measurement.

Referring to FIG. 5, the teeth 30 of the malocclusion models 20, 22 are separated from their respective base support 32. This is typically done by a grinding or cutting operation. As illustrated in FIG. 5, this cutting operation can be accomplished by a large fiberglass disc 33.

Referring to FIG. 6, the individual teeth 30 are shown separated from its respective base support 32. The top surface 34 of base support 32 is provided with a plurality of grooves 36 in a cross-hatch pattern as illustrated. The grooves 36 may be simply formed by a large disc which cuts a narrow groove 36 therein. This cross-hatch pattern helps insure that the wax to be used for arranging the teeth will adhere and remain during the remaining steps of the present invention.

Figure 7:
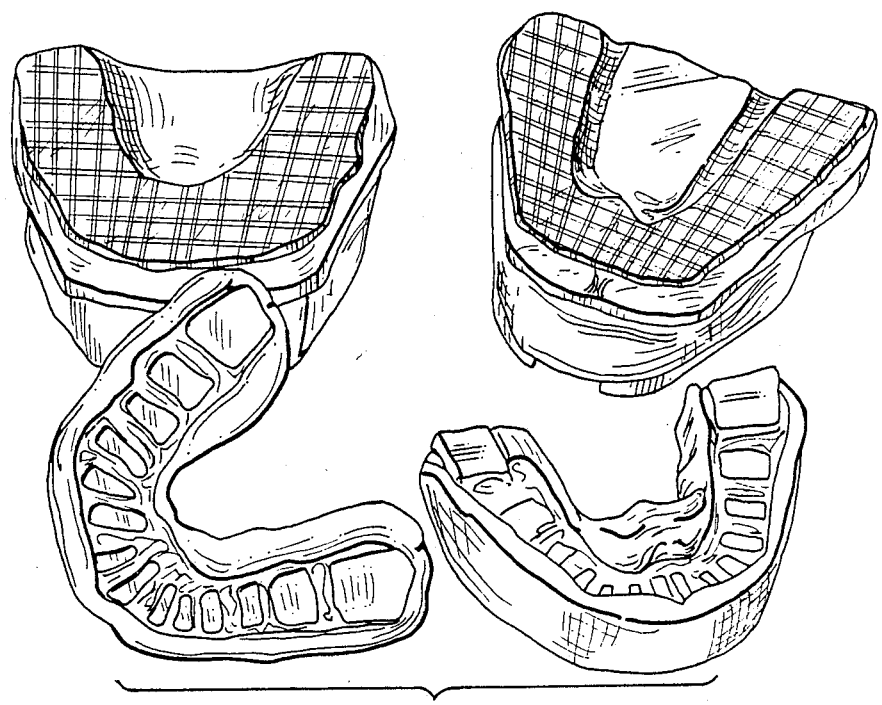
FIG. 7 is a perspective view of the base portions of FIG. 6 and the individual teeth in its respective support tray wax filled.
Figure 8:
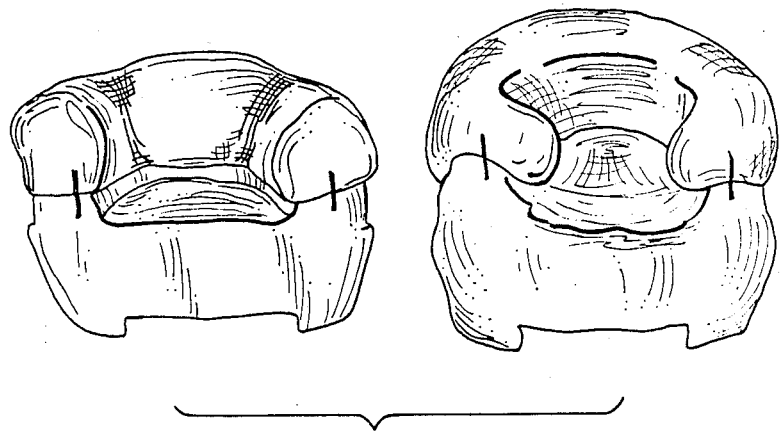
FIG. 8 is a back elevational view illustrating the tray and respective individual teeth placed over its respective base portion.

Referring to FIG. 7, each of the teeth 30 are returned to its appropriate corresponding positions in its respective silicone putty tray 24, 26 previously made. The individual teeth have been trimmed such that a small amount of clearance is provided around each tooth at its base 38 (see FIG. 6). Wax 40 is then poured between the teeth and tray 24, 26. Additionally, a thin layer of wax is provided to the upper surface 34 of base support 32. The silicone trays 24, 26 are then each placed upon its respective base support 32. The wax in the silicone tray and on the model is warmed and united using the upper end 28 and reference line 29 as guides for proper alignment. The silicone trays 24, 26 are then removed from the wax malocclusion model 20, 22. The teeth 30 are now back in the maloccluded position.

The teeth 30 in wax are then moved from the maloccluded position in accordance with the appropriate orthodontist's prescription to provide a functional esthetic orthodontically achievable position. This is accomplished by appropriately heating portions of the wax, and then moving the teeth in accordance with the desired prescription. It can be seen that the teeth are moved directly from the malocclusion position to its prescribed arrangement. This avoids or minimizes the placing of the teeth in an ideal position which may be difficult to obtain or possibly is not achievable. While in the preferred embodiment, as illustrated, wax is used as the medium to hold the individual teeth and allow movement to the ideal or prescribed form, any other medium may be used, for example, but not by way of limitation, modeling clay could be used.

In order to assist in establishing the ideal arch form, an arch forming tool 40 is used. The tool 40 comprises a pair of blade forms 42 which are held in position by a clamping base 44 which has a slot 46 for receiving the pair of blade forms 42. The pair of blade form 42 comprises two individual pieces which are the mirror image of the other and when placed together provide an arch form. A pair of locking screws 48 are secured to base 44 such that as the locking screws are turned it will securely hold the blade forms 42 therein. The base 44 is also provided with a mounting rod 50 which is used to manipulate the arch forming tool 40 either by hand or in a tool support such as a parallelometer. The blade forms 42 have a peripheral edge 52 which is designed to provide and establish an arch form. The blade forms 42 may be moved within the base 44 to a variety of positions so as to provide a wide variety of desired arch forms. Applicants have found that approximately five different peripheral edge configurations will provide approximately 90 percent of all arch forms desired. While in the present invention the blade forms 42 are illustrated as being two separate pieces, the blade forms 42 may be a single piece construction, however, this would require a considerable number more blade forms to accommodate the various arch forms required.

Therefore, the blade forms are provided as two separate pieces as illustrated. In the particular embodiment illustrated, the blade forms 42 are for the placement of brackets on the labial side, however, in like manner, desired arch forms may be configured for lingual brackets and arch forms.

The blade forms 42 have a thickness (T) designed to fit within the slot of an orthodontic bracket. The tool 40 is placed in a parallelometer and is used to establish the arch wire plane. Additionally, the tool 40 may be used for a trial placement of the orthodontic brackets to insure that the arch form will allow placement of the brackets within the parameters of the bracket design and the thickness of the filling material placed on the base pads of the bracket.

Figure 12:
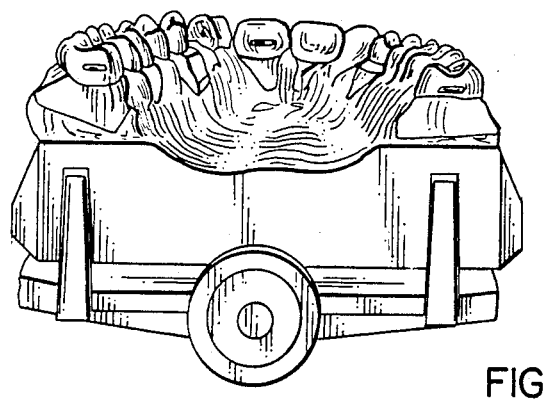
FIG. 12 is a back elevational view of one of a model with the arch wire plane marked.

Referring to FIG. 12, the arch wire plane is marked by placing parallel grooves 59 cut into the model 20, 22. This will allow the orthodontist or technician to reestablish the arch wire plane at a later time.

The maxillary and mandibular malocclusion models 20, 22 are then removed from the mounting devices and any additionally corrections that need to be made to the teeth can be made at this time. For example, overbite, over-rotation, setback, etc.

The models 20, 22 are remounted to the T.A.R.G. device and then each tooth is remeasured for angulation, torque and the results recorded. Additionally, the position of the teeth with respect to overbite, overjet, midline, innercanine, and inner molar width are also recorded in this way. Now the technician and/or orthodontist may readily determine how much change will occur from the malocclusion to the desired prescription as illustrated in the following Table B.

TABLE B

CASE ANALYSIS
PATIENT SIZE JANE DOE    c 2000

| TOOTH | MALOCCLUSION | | R$_x$OCCLUSION | | DEGREE CHANGE | |
|---|---|---|---|---|---|---|
| | TQ | ANG | TQ | ANG | TQ | ANG |
| UPPER | | | | | | |
| CENTRAL-R | +1 | +3 | +15 | +5 | +8 | +2 |
| CENTRAL-L | +8 | +3 | +14 | +5 | +6 | +2 |
| LATERAL-R | +5 | +7 | +10 | +8 | +5 | +1 |
| LATERAL-L | +6 | +8 | +10 | +8 | +4 | +2 |
| CUSPID-R | −8 | +5 | −4 | +9 | +4 | +4 |
| CUSPID-L | −5 | +9 | −2 | +9 | +3 | 0 |
| LOWER | | | | | | |
| CENTRAL-R | −3 | −4 | +1 | 0 | +4 | +4 |
| CENTRAL-L | 0 | +1 | +1 | 0 | +1 | −1 |
| LATERAL-R | −4 | −8 | +1 | +3 | +5 | +11 |
| LATERAL-L | −4 | −2 | +1 | +4 | +5 | +6 |
| CUSPID-R | −9 | −1 | −7 | +5 | +2 | +6 |
| CUSPID-L | −9 | −3 | −6 | +4 | +3 | +7 |

| OTHER CONSIDERATIONS | | | |
|---|---|---|---|
| | MALOCCLUSION | R$_x$OCCLUSION | CHANGE |
| OVERSET | 7 mm | 1 mm | −6 mm |
| OVERBITE | 4 mm | 1 mm | −3 mm |
| INTERCANINE WIDTH (MANDIBULAR) | 23 mm | 25 mm | +2 mm |
| INTERMOLAR WIDTH (MANDIBULAR) | 40 mm | 40 mm | NO CHANGE |
| DENTAL MIDLINE | ON | ON | NO CHANGE |

Figure 13:
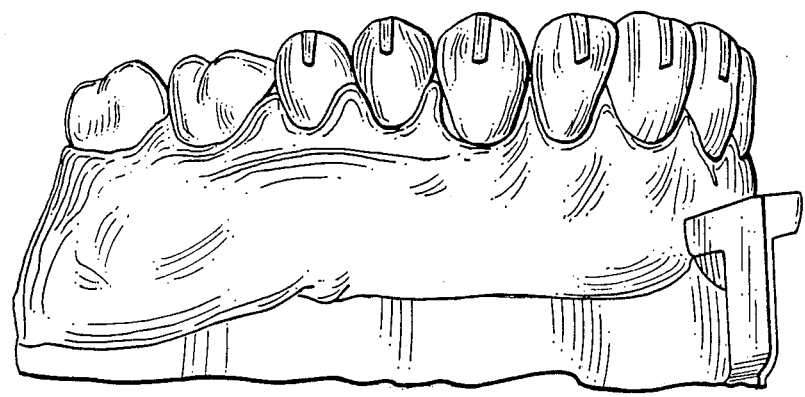
FIG. 13 is a side elevational view of the maxillary model illustrating the locating grooves filled in with an adhesive.

The teeth are now in their ideal form in the maxillary, mandibulary malocclusion model. A duplicate model 54 is now made of the wax model 20, 22 as illustrated in FIG. 13. A dilute solution of a foil substitute is applied to the surface of the duplicate model 54. The duplicate models are then dried in a 200° oven for five minutes to bake the foil substitute into the duplicate model rather than have it as an addition to the model surface. This material will return to the surface of the duplicate model 54 when soaked in water and release the cured fill material from the duplicate model 54.

Figure 14:
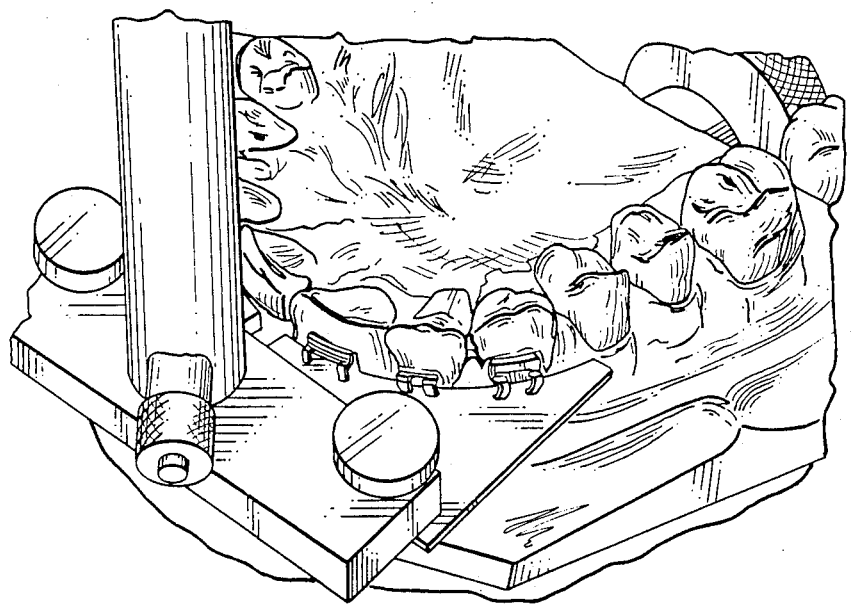
FIG. 14 is a perspective view of the maxillary model illustrating how the brackets of the four incisors are placed in their final position.

The duplicate model 54 is placed in an adjustable model holder and the arch wire plane is reestablished. This can be simply done by using the previously cut grooves 59. When all the grooves 59 are placed in the same plane, the arch wire plane is reestablished. Then, a trial placement of the brackets is conducted to insure proper placement and fit. Prior to placement of the brackets, all locating grooves 12 are filled with a layer of a thermal cure fill material 56. In the particular embodiment illustrated fill material 56 is dimethacralate, however, any other desired thermal cure material may be used. The use of a thermal cure fill material allows for sufficient time to accurately place the brackets or modify the position of the bracket to the prescribed position. Preferably, this material is of a different color to insure accurate removal when it serves its purpose of relocating the bracket on the maloccluded model 10. This fill material is loaded onto the base of the bracket and then is placed on the tooth. Preferably, this is done through the use of a tool 40 mounted to a parallelometer. The bracket is simply lightly placed against a tooth. The fill material 56, at this point, is not fully expressed. After the brackets have been mounted to the four incisors, the arch form tool 40 is used to finally place the brackets and fully express the fill material from all the incisors brackets at the same time so as to conform with the arch form previously established (see FIG. 14). By using the tool 40, at least two brackets are placed at the appropriate position with respect to its respective tooth. This same procedure is conducted for the bicuspids using a blade form which corresponds to the arch wire form and then last the molar brackets are placed using a common blade.

Figure 15:
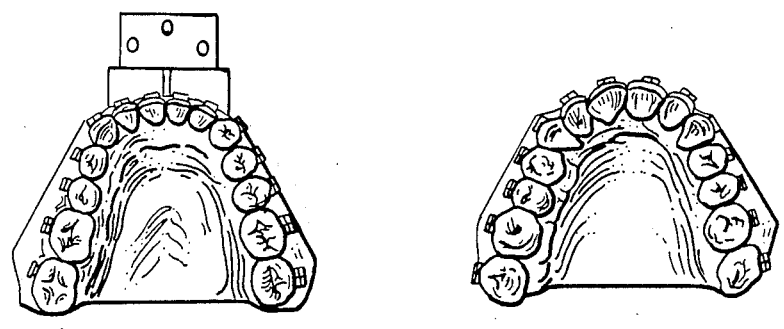
FIG. 15 illustrates two photographs of the brackets as placed on the ideal working model and illustrates the arch forming device in position to illustrate the actual ideal arch form.

After the brackets have been placed on the teeth, any excess fill material around the base of the bracket is then removed. The fill material is cured in a conventional oven for approximately one hour at 105° C. Additional time may be needed for extra thick adhesive as needed. A one-to-one photograph is taken of the cured brackets on the duplicate model 54 (see FIG. 15).

The tool 40 with the predetermined arch form which was used to place the brackets on the model 54 is now used to trace the arch wire template. This is accomplished by placing the tool 40 with the blade forms in the brackets and taking a photograph (see FIG. 15). Then, an arch wire templated is made by identifying the slots in each bracket by dashes and connecting these dashes much the same was as connecting numbered dots to form pictures we did as children.

The duplicate model 54 with cured custom bracket bases is submerged in the water for two or three minutes to loosen the cured fill material from the model 54. Each individual bracket is then removed and is placed on the malocclusion 10. At this point in time, each bracket 60 has a fill material base 61 as illustrated in FIG. 17. The bracket 60 is placed in its corresponding position on the malocclusion model. As can be seen in FIG. 17, each bracket has a projection 64 which corresponds to the locating groove. Therefore, when the bracket 60 is taken from the duplicate model 54 and placed in the malocclusion model 54, it can be accurately placed in position on the tooth. Due to the well defined seat 14, it is quite evident when the bracket is not properly seated. This procedure is repeated until all the brackets are taken from the duplicate model 54 and placed on the malocclusion 10.

Figure 16:
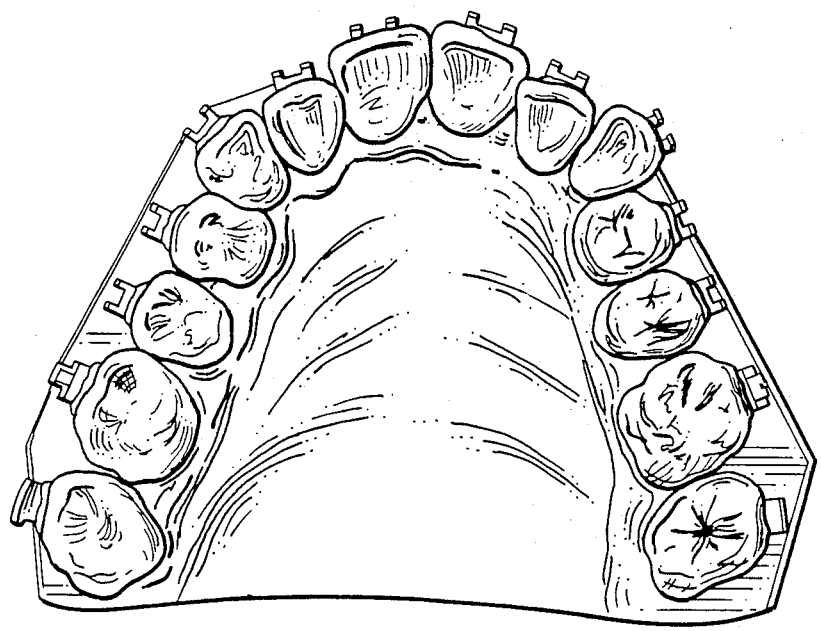
FIG. 16 illustrates a top plan view of the maxillary model of figure with the bracket placed thereon.

A one-to-one picture of the brackets in the malocclusion 10 is taken (see FIG. 16). This photo can be used to pre-bend arch wires, determine what teeth are bracketed, illustrate what the brackets will look like after bonding and various other uses.

The brackets may be transferred to the patient in any desired manner. In one form, a bioplast tray 60 is formed over malocclusion 10 is made. (See FIG. 18). The projections formed by the locating groove is removed. This can be easily accomplished by using a round carbide burr. Since only a very small portion of the bracket is affected, the accuracy of removal of the projection is excellent.

Another method for removing and transferring the brackets that can be used is a silicone putty overtray (not shown). This type of tray gives more seating support and serves to store the inner bioplast tray which can be used for the rebonding of individual bracket as required. Alternatively, another tray option is an all silicone putty tray (not shown). This tray could be constructed of a light body and a heavy body silicone. Sometimes a hard outer shell is prescribed.

The brackets in their appropriate transfer medium are taken from the malocclusion model. The brackets are cleaned in an ultrasonic cleaning machine and brushed with an acetone. This procedure is insured to provide a clean bonding surface to the base of the bracket. Generally, a light, almost dry coat is applied to the base of the bracket as a surface conditioner. The brackets are then applied to the patient as typically done in the prior art.

It is to be understood that the various changes and modifications may be made without departing from the scope of the present invention.

What is claimed is:

1. A method for constructing an orthodontic appliance to be placed in a patient's mouth so as to effect the desired tooth repositioning, comprising the steps:
   (a) forming a model of a patient's malocclusion;
   (b) establishing a locating groove in each tooth of said patient's malocclusion;
   (c) determining and recording the position of each of said tooth in said malocclusion;
   (d) separating said teeth from said model and placing said teeth back in their malocclusion positions on a base support whereby said teeth are capable of being manipulated in said support;
   (e) moving said teeth to their prescribed positions on said base support;
   (f) determining and recording the position of each of said teeth in their prescribed position;
   (g) establishing the desired arch form for said teeth;
   (h) placing orthodontic brackets on said teeth in accordance with said desired arch form; and
   (i) transferring said orthodontic brackets to a second model of the patient's malocclusion using said locating groove.

2. A method for constructing an orthodontic appliance to be placed in a patient's mouth so as to effectuate the desired tooth repositioning, comprising the steps of:
   (a) forming a model of a patient's malocclusion;
   (b) establishing a locating groove in each tooth of said patient's malocclusion;
   (c) separating said teeth from said model and placing said teeth back in their malocclusion positions on a base support whereby said teeth are capable of being manipulated in said support;
   (d) moving said teeth into their prescribed position on said support;
   (e) placing orthodontic brackets on said teeth; and
   (f) transferring said orthodontic brackets to a second model of the patients malocclusion using said locating groove.

3. A method for constructing an orthodontic appliance to be placed in a patient's mouth so as to effectuate the desired tooth repositioning, comprising the steps of:
   (a) forming a model of a patient's malocclusion;
   (b) establishing a locating groove of each tooth of said patient's malocclusion;
   (c) moving said teeth into their prescribed positions on said support;
   (d) establishing the desired arch form for said teeth; and
   (e) placing orthodontic brackets on said teeth in accordance with said desired arch form using said locating groove.

4. A method for constructing an orthodontic appliance to be placed in a patient's mouth so as to effect the desired tooth repositioning, comprising the steps:
   (a) forming a model of a patient's malocclusion;
   (b) establishing a locating groove of each said tooth of said patient's malocclusion;
   (c) determining and recording the position of each of said tooth in said malocclusion:
   (d) separating said teeth from said model and placing said teeth back in their malocclusion positions on a base support whereby said teeth are capable of being manipulated in said support;
   (e) moving said teeth into their prescribed position on said support;
   (f) determining and recording the position of each of said teeth in their prescribed position; and
   (g) placing orthodontic brackets on said teeth in accordance with said desired arch form using said locating groove.

* * * * *